United States Patent
Öhman et al.

(10) Patent No.: US 10,934,579 B2
(45) Date of Patent: *Mar. 2, 2021

(54) USE OF A POROUS CAPILLARY MEMBRANE FOR DETERMINING THE AMOUNT OF ROLLING CIRCLE AMPLIFICATION PRODUCTS

(71) Applicant: Vanadis Diagnostics, Sollentuna (SE)

(72) Inventors: Ove Öhman, Uppsala (SE); Fredrik Persson, Uppsala (SE); Mathias Howell, Uppsala (SE)

(73) Assignee: VANADIS DIAGNOSTICS, Sollentuna (SE)

(*) Notice: Subject to any disclaimer, the term of this patent is extended or adjusted under 35 U.S.C. 154(b) by 191 days.

This patent is subject to a terminal disclaimer.

(21) Appl. No.: 16/246,155

(22) Filed: Jan. 11, 2019

(65) Prior Publication Data

US 2019/0211383 A1 Jul. 11, 2019

Related U.S. Application Data

(63) Continuation of application No. 15/144,468, filed on May 2, 2016, now Pat. No. 10,208,336.

(30) Foreign Application Priority Data

Apr. 30, 2015 (GB) .................................. 1507376

(51) Int. Cl.
*C12Q 1/68* (2018.01)
*C12Q 1/6844* (2018.01)
*C12Q 1/6834* (2018.01)

(52) U.S. Cl.
CPC ......... *C12Q 1/6844* (2013.01); *C12Q 1/6834* (2013.01)

(58) Field of Classification Search
CPC combination set(s) only.
See application file for complete search history.

(56) References Cited

U.S. PATENT DOCUMENTS 5,854,033 A 12/1998 Lizardi
10,208,336 B2 * 2/2019 Ohman ................ C12Q 1/6834
(Continued)

FOREIGN PATENT DOCUMENTS

CN 102146460 8/2011
CN 102827929 6/2014
(Continued)

OTHER PUBLICATIONS

Sato et al. (Lab Chip 2010, 10, p. 1262-1266) (Year: 2010).*
(Continued)

*Primary Examiner* — Stephanie K Mummert
(74) *Attorney, Agent, or Firm* — James S. Keddie; Bozicevic, Field & Francis LLP (57) ABSTRACT

A method of sample analysis is provided. In certain embodiments, the method may comprise: (a) filtering a liquid sample containing rolling circle amplification (RCA) products using a porous capillary membrane, thereby producing an array of the RCA products on the membrane; wherein the sample contains at least a first population of RCA products and a second population of RCA products, wherein the first and second populations of labeled RCA products are distinguishably labeled; and (b) determining the amount of the first labeled population of RCA products and the amount of the second labeled population of RCA products in an area of the membrane.

20 Claims, 5 Drawing Sheets

(56) References Cited

U.S. PATENT DOCUMENTS

| | | | |
|---|---|---|---|
| 2003/0096268 | A1 | 5/2003 | Weiner et al. |
| 2003/0219765 | A1 | 11/2003 | Costa |
| 2004/0115674 | A1 | 6/2004 | Knott et al. |
| 2005/0009022 | A1* | 1/2005 | Weiner ............. B01J 19/0046 435/6.12 |
| 2006/0134397 | A1 | 6/2006 | Smith |
| 2006/0228813 | A1 | 10/2006 | Wu et al. |
| 2008/0167198 | A1* | 7/2008 | Cooney ............. G01N 21/6452 506/7 |
| 2010/0047773 | A1 | 2/2010 | Erland et al. |
| 2013/0323729 | A1 | 12/2013 | Zhejiang |

FOREIGN PATENT DOCUMENTS

| | | |
|---|---|---|
| JP | 2004526432 | 9/2004 |
| JP | 2005520484 | 7/2005 |
| WO | WO2002057487 | 7/2002 |
| WO | 6/02003004690 | 1/2003 |
| WO | 20110142836 | 11/2011 |
| WO | 20120019200 | 2/2012 |
| WO | 2015083001 | 6/2012 |
| WO | 2015083002 | 6/2015 |

OTHER PUBLICATIONS

Whatman Anodisc, WHA68095012; 2018, p. 1-3 (Year: 2018).*
Goransson et al. (PLoS One, 2012, 7(2):e31068, p. 1-9) (Year: 2012).*
Durtschi et al., "Increased sensitivity of bacterial detection in cerebrospinal fluid by fluorescent staining on low-fluorescence membrane filters" Journal of Medical Microbiology, 2005, pp. 843-850, vol. 54.
Ingham et al., "Where bio meets nano: The many uses for nanoporous aluminum oxide in biotechnology" Biotechnology Advances, 2012, pp. 1089-1099, vol. 30.
Poinern et al., "Progress in Nano-Engineered Anodic Aluminum Oxide Membrane Development" Materials, 2011, pp. 487-526, vol. 4.
Santos et al., "Nanoporous anodic aluminum oxide for chemical sensing and biosensors" Trends in Analytical Chemistry, Mar. 2013, p. 25-38, vol. 44.
Tanaka et al., "Single-Molecule DNA Patterning and Detection by Padlock Probing and Rolling Circle Amplification in Microchannels for Analysis of Small Sample Volumes" Analytical Chemistry, 2011, pp. 3352-3357, vol. 83.
Van Beuningen et al., "Fast and specific hybridization using flow-through microarrays on porous metal oxide" Clinical Chemistry, 2001, pp. 1931-1933, vol. 47.
Nilsson et al., "Real-time monitoring of rolling-circle amplification using a modified molecular beacon design", Nucleic Acids Research, 2002, 30(14): e66.
Tanner et al., "Real-time single-molecule observation of rolling-circle DNA replication", Nucleic Acids Research, 2009, 37(4):e27.
Reirß et al., "Synthesis and Stretching of Rolling Circle Amplification Products in a Flow-Through System", Small, 2009, 5(20):2316-2322.
Nhatman Anodisc (see WHA68095012; 2018, p. 1-3).

* cited by examiner

USE OF A POROUS CAPILLARY MEMBRANE FOR DETERMINING THE AMOUNT OF ROLLING CIRCLE AMPLIFICATION PRODUCTS

CROSS-REFERENCING

This application is a continuation of U.S. application Ser. No. 15/144,468, filed on May 2, 2016, which claims the benefit of UK Patent Application Serial No. 1507376.0, filed on Apr. 30, 2015, which applications are incorporated herein for all purposes.

BACKGROUND

Non-invasive prenatal testing provides information about the condition or health of a fetus using a maternal blood sample or another sample obtained non-invasively from the pregnant female. Early detection of the condition or health of the fetus allows targeted interventions and medical treatments.

Rolling-circle amplification (RCA) is useful for analyzing cell free DNA in maternal blood. However, quantifying RCA products with statistical robustness can be challenging. At a practical level, although the absolute numbers of products in an RCA reaction may be sufficiently high to provide statistical robustness, the molar concentration of specific RCA amplicons in the reaction may be quite low, which limits the types of methods that one can use to quantify them. For example, RCA products in a sample can, in theory, be detected by labeling the RCA products, depositing the sample onto the surface of a glass slide, and counting the number of labeled products on the slide. However, simply placing a solution containing labeled RCA products on a glass slide, allowing the labeled RCA products to diffuse to the surface and then counting the number of labeled RCA products that have attached to the slide takes several hours and not all of the labeled RCA products reach the slide and are counted.

Use of filtration onto a solid support to quantify labeled RCA products is described herein. As will be described in greater detail below, the methods may facilitate analysis of samples containing RCA products.

SUMMARY

A method of sample analysis is provided. In certain embodiments, the method may comprise: (a) filtering a liquid sample containing rolling circle amplification (RCA) products using a porous capillary membrane, thereby producing an array of the RCA products on the membrane; wherein the sample contains at least a first population of RCA products and a second population of RCA products, wherein the first and second populations of labeled RCA products are distinguishably labeled; and (b) determining the amount of the first labeled population of RCA products and the amount of the second labeled population of RCA products in an area of the membrane. In some embodiments, the determining step may include counting the number of first and second labeled RCA products in the area. In other embodiments, the determining step may include detecting an aggregate signal from the area. Either way, the method can provide an estimate of the number of first and second populations of RCA products in the sample.

Depending on how the method is implemented, use of the porous capillary membrane can enable quantification of substantially all RCA products in a sample (not just the ones that happen to diffuse to the surface of the glass slide) and this, in turn, increases the precision, sensitivity and reproducibility of the assay. Moreover, use of the porous capillary membrane allows the assay to be done in minutes rather than hours as compared to some alternative methods, which, as noted above, can rely on pipetting a sample onto a glass slide and then incubating the slide for an extended period of time in the hope that the RCA products will diffuse and stick to the surface of the slide. Consistent with this, the experimental section of the present application reports that practice of the present method can result in at least a 2.5-fold more RCA products being counted after 90 seconds (which equals the time taken to place the sample on top of the membrane and then draw the sample through the membrane) as compared to the an incubation of 16 hours on a glass slide. In addition, use of the membrane can reduce background by allowing the potential sources of background (e.g., fluorescent oligonucleotide molecules that have not hybridized to an RCA product, or the like) to pass through the membrane (particularly if the membrane is washed after the RCA products have been applied).

The method finds particular use in analyzing samples that have a relatively wide range of concentrations of RCA products (e.g., 10 to 10M RCA products in a volume of 50 µl to 200 µl or more) that in many cases may have a relatively low concentration because, as mentioned above, the membrane serves to concentrate the RCA products on the surface of the membrane. Put another way, without using the membrane and instead using an alternative approach, a 50 µl sample would spread over the surface of a glass microscope slide and, even if all of the RCA products could be induced to bind to the slide, the RCA products would so spatially separated from one another on the slide that a single field of view would only contain an insufficient number of RCA products, thereby making it time consuming and inefficient to quantify them by microscopy or other means with any reasonable accuracy. Depending on how the method is implemented, the membrane may serve to concentrate and support the RCA products while, at the same time, providing a means by which the RCA products can be washed in order to decrease background. In addition, the membrane can serve as a microscopy slide, particularly if it is transparent or can be made transparent by addition of a wetting agent.

In sum, the present method is believed to provide a fast, highly precise, sensitive and reproducible way to determine the amount of RCA products—a product that itself is already made without bias in the sense that each target molecule is represented by only one RCA product (in contrast to PCR in which each target molecule is amplified into an unknown number of copies and the different target molecules are amplified by different amounts)—in a sample. As such, the present method should prove to be invaluable for applications in which fast, precise and accurate measurements of the abundance of DNA molecules in a sample are essential. In particular, the present method should prove to be valuable for non-invasive prenatal testing, where fast, precise and accurate measurements of the abundance of relatively low concentration DNA molecules that are in the cell free fraction of the maternal bloodstream are critical.

These and other potential features and advantages may become apparent in view of the following description.

BRIEF DESCRIPTION OF THE FIGURES

The skilled artisan will understand that the drawings, described below, are for illustration purposes only. The drawings are not intended to limit the scope of the present teachings in any way.

DETAILED DESCRIPTION

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, the some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

Before describing exemplary embodiments in greater detail, the following meanings are set forth to illustrate the meaning and scope of the terms used in the description.

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

As used herein, the term "filtering" includes the act of moving a liquid that contains analytes (e.g., rolling circle amplification products) through a filter such that some of the analytes are retained by the filter. In filtering, at least some of the liquid is transferred from one side of the filter to the other.

As used herein, the term "rolling circle amplification" or "RCA" includes an isothermal amplification that generates linear concatemerized copies of a circular nucleic acid template using a strand-displacing polymerase. RCA is well known in the molecular biology arts and is described in a variety of publications including, but not limited to Lizardi et al (Nat. Genet. 1998 19:225-232), Schweitzer et al (Proc. Natl. Acad. Sci. 2000 97:10113-10119), Wiltshire et al (Clin. Chem. 2000 46:1990-1993) and Schweitzer et al (Curr. Opin. Biotech 2001 12:21-27), which are incorporated by reference herein.

As used herein, the term "rolling circle amplification products" includes the concatamerized products of a rolling circle amplification reaction. As used herein, the term "fluorescently labeled rolling circle amplification products" refers to rolling circle amplification products that have been fluorescently labeled by, e.g., hybridizing a fluorescently labeled oligonucleotide to the rolling circle amplification products or other means (e.g., by incorporating a fluorescent nucleotide into the product during amplification).

As used herein, the term "porous capillary membrane" includes membranes that have relatively densely packed individual capillaries that span the thickness of the membrane, i.e., that go from one side of the membrane to the other, thereby allowing the passage of liquid, but not particles, from one side of the membrane to the other. Examples of porous capillary membranes include, but are not limited to, e.g., anodic aluminum oxide membranes (see below), nanochannel glass membranes, track etched membranes and polytetrafluoroethylene. Nanochannel glass membranes are made of glass and have a high density of uniform channels with diameters from 15 microns to 15 nanometers (see, e.g., Tonucci et al., Advances in Nanophotonics II, AIP Conference Proceedings, 2007 959: 59-71; Pearson et al, Science 1995 270: 68-70 and Tonucci et al., Science 1992 258: 783-785, as well as U.S. Pat. Nos. 5,306,661; 5,332,681; 5,976,444; 6,087,274; 6,376,096; 6,483,640; and 6,599,616, which are incorporated by reference). Track etched membranes are made of a transparent polymer (e.g., polycarbonate, polyethylene terephthalate or polyimide and the like) containing pores having a diameter in the range of 0.01 um to 30 um that have been made by a combination of charged particle bombardment (or irradiation) and chemical etching. Other porous membranes of interest include, but are not limited to amorphous fluoropolymers such as NAFION™, TEFLON AF™, FEFLON FEIP™, and CYTOP™ (DuPont Fluoroproducts, Fayetteville, N.C.). As would be recognized, a porous capillary membrane may have a surface (e.g., a coating or a chemically modified surface) that is different to the material from which the membrane is made. For example, the surface of a porous capillary membrane may have an altered charge characteristics or altered hydrophobicity or hydrophilic characteristics. In some embodiments, the surface may be coated with amino silane, polylysine or another compound to provide a positive charge that helps retain the RCA products to the surface. Alternatively or in addition, the surface may have a thin layers of a metal (e.g., titanium, gold) deposited therein, which can be linked to other agents that modify the surface properties of the filter.

As used herein, the term "anodic aluminum oxide membrane" includes a regular, self-organized nanoporous membranous structure that is produced when Al is anodized in certain acidic media. The interior diameter of the pores in the membrane, the distance between the centers of adjacent pores in the membrane, and the distance between the edges of adjacent pores in the membrane can be controlled by the voltage of the deposition, the type of acid, and other parameters. An anodic aluminum oxide membrane is virtually transparent when wet. Anodic aluminum oxide membrane, its properties, and how to make such membranes are reviewed in in detail in a variety of publications including, but not limited to: Li et al (Chem. Mater 1998 10: 2470-2480), Santos et al (Trends on Analytical Chemistry 2013 44: 25-38), Ingham et al (Biotechnology Advances 30 2012 1089-1099) and Poinern et al. (Materials 2011 4: 487-526), which are incorporated by reference herein for those teachings. Anodic aluminum oxide membranes are commercially available under the tradename ANOPORE™ from, e.g., SPI Supplies (West Chester, Pa.) and from other vendors such as Sykera Technolgoies Inc (Longmont, Colo.) and Signma-Aldrich (St. Louis, Mo.) and can be purchased with a support ring.

As used herein, the term "area", in the context of an area of a membrane or an area of an image, includes a contiguous or non-contiguous area. For example, if a method involves determining the amount of labeled RCA products in an area, e.g., counting the number of labeled RCA products in an area, the area in which the RCA products are quantified may be a single, contiguous space or multiple non-contiguous spaces.

As used herein, the term "imaging" includes a process by which optical signals from the surface of an object are detected and stored as data in association with a location (i.e., a "pixel"). A digital image of the object can be reconstructed from this data. An area of a membrane may be imaged using a single image or one or more images.

As used herein, the term "individual labeled RCA products" includes individual RCA molecules that are labeled.

As used herein, the term "determining the amount" includes methods in which individually resolved RCA products are counted as well as methods that include measuring an aggregate signal from multiple RCA products. In methods that involve measuring the intensity of an aggregate signal, the individual RCA products do not need to be resolved. The amount of RCA products can be expressed using any suitable unit. In some cases, the amount of RCA products may be expressed as the number of individually resolved RCA products that have been counted.

As used herein, the term "counting" includes determining the number of individual objects in a greater collection. In embodiments, "counting" requires detecting separate signals from individual objects in a plurality (not a collective signal from the plurality of objects) and then determining how many objects there are in the plurality by counting the individual signals. In the context of the present methods, "counting" may be performed by determining the number of individual signals in an array of signals.

As used herein, the term "transparent" includes a state in which an object is optically transparent at the wavelength being used. For fluorescence microscopy, "transparent" means that the object will be transparent to one or both of the excitation and emission spectra of a fluorophore. As will be described in greater detail below, certain membranes are transparent only when they have been wetted. Such membranes are considered transparent membranes even though the dry form of those membranes may not be transparent.

As used herein, the term "array" with reference to an array of RCA products includes a collection of single RCA products on a planar surface, where the RCA products are spatially separated from one another on the plane of the surface (to the extent allowed by Poisson distribution of the array is truly random). A "random" array includes an array wherein the elements, e.g., RCA products, are distributed on the surface of a substrate at positions that are not predetermined. In some cases, the distribution of RCA products on a random array may be described by Poisson statistics, such that, e.g., the distribution of distances between RCA products of a random array can be approximated using a Poisson distribution. In other words, the RCA products may be distributed randomly, i.e., at no pre-determined locations, on a membrane Other meanings of these and other terms may appear throughout the specification.

Prior to describing the present method in more detail, it is recognized that the present method can be implemented using any type of capture support that can act as a filter for RCA products. Such capture supports should have a low background signal at the wavelengths used in analysis and a pore size sufficient to allow rapid fluid flow-through of liquid and capture RCA products. Suitable capture supports may be made from porous organic or inorganic materials including solids such as porous metals, ceramics, homogeneous films (e.g., polymers) and heterogeneous solids (polymeric mixes, mixed glasses). Porous ceramic membranes can be made from inorganic materials (such as alumina, titania, zirconia oxides, recrystallized silicon carbide). See, e.g., the PamChip sold by Pamgene (The Netherlands), Wu et al, Nucleic Acids Res. 2004 32: e123 and Anthony et al Biotechniques. (2003) 34:1082-6, 1088-9. Exemplary porous polymer membranes can be made from cellulose acetate, nitrocellulose, cellulose esters (CA, CN, and CE), polysulfone (PS), polyether sulfone (PES), polyacrilonitrile (PAN), polyamide, polyimide, polyethylene and polypropylene (PE and PP), polytetrafluoroethylene (PTFE), polyvinylidene fluoride (PVDF) and polyvinylchloride (PVC). As such, in some embodiments, the method may comprise: (a) filtering a liquid sample containing rolling circle amplification (RCA) products using a capture support that acts as a filter for the RCA products, thereby producing an array of the RCA products on the support; wherein the sample contains at least a first population of RCA products and a second population of RCA products, wherein the first and second populations of labeled RCA products are distinguishably labeled; and (b) determining the amount of the first labeled population of RCA products and the amount of the second labeled population of RCA products in an area of the membrane.

The description that follows below illustrates an implementation in which a porous capillary membrane is used. Porous capillary membranes are an example of a capture support that could be used. The following description illustrates the present method by example.

Figure 1:
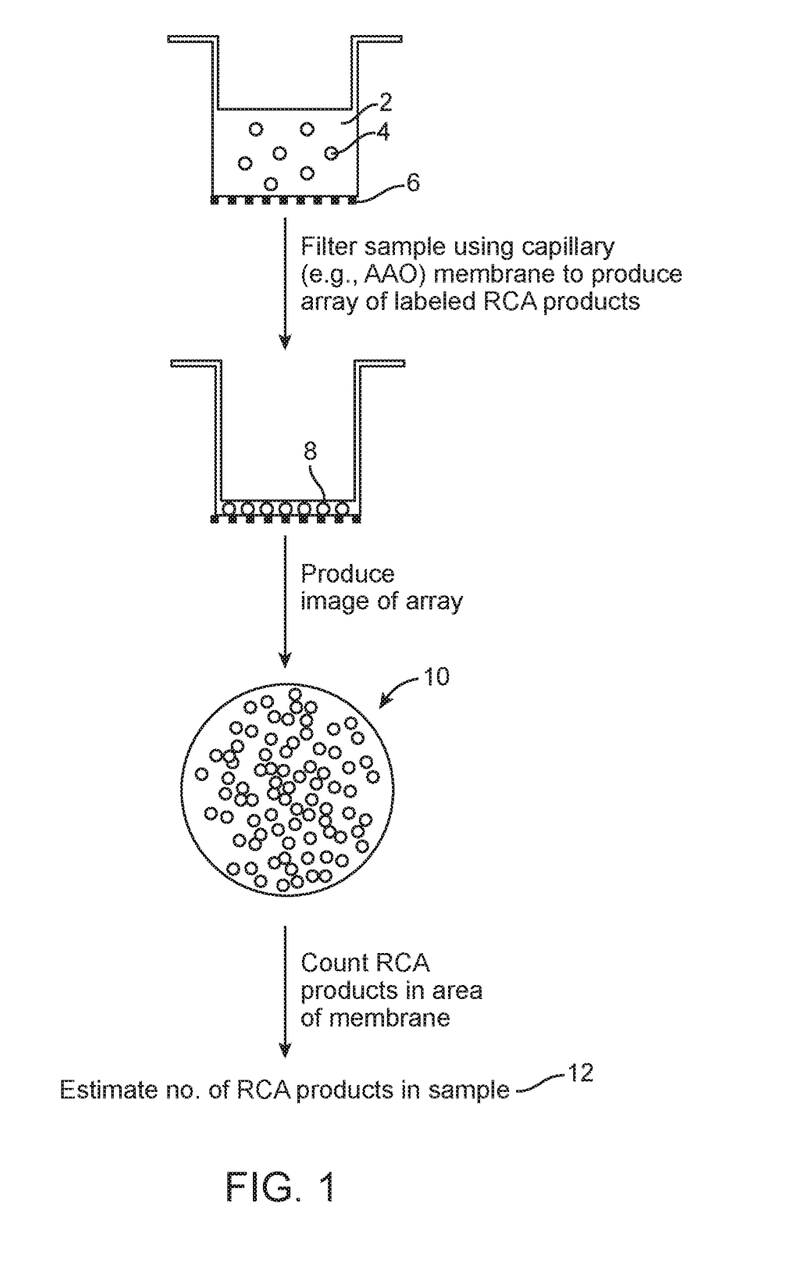
FIG. 1 schematically illustrates some of the steps of the present method.

As summarized above, a method of sample analysis is provided. In certain embodiments, the method may comprise: (a) filtering a liquid sample containing rolling circle amplification (RCA) products through a porous capillary membrane, thereby producing an array of the RCA products on the membrane; (b) fluorescently labeling the RCA products prior to or after step (a); and (c) determining the amount of the individual labeled RCA products in an area of the membrane, thereby providing an estimate of the number of the labeled RCA products in the sample. The method may be performed in a variety of different ways, one implementation of which is schematically illustrated in FIG. 1. With reference to FIG. 1, certain embodiments of the method involve: filtering a liquid sample 2 containing fluorescently labeled rolling circle amplification (RCA) products 4 through a porous capillary membrane 6 (e.g., an anodic aluminum oxide membrane). The filtering step concentrates the particles and results an array of the RCA products 8 on membrane 6. In the illustrated embodiment, the next step involves detecting the particles while they are on the membrane. In some embodiments, this step may produce image 10 of array 8. As would be apparent, the detecting may be done any suitable fluorescence detector, e.g., a fluorescence microscope, a scanner, using a high resolution CMOS or CCD detector or using a PMT or the like. Finally, the amount of labeled RCA products in the area of the membrane is determined, e.g., by counting individually resolved RCA products, or by measuring an aggregate signal, etc. This determination provides an estimate of the number of the labeled RCA products 12 in sample 2. In certain embodiments and depending on how the method is performed, the filter may be wetted, e.g., with a wetting agent (e.g., an immersion oil or glycerol) to wet the membrane and make it transparent). In these embodiments, the porous capillary membrane may be made transparent using a wetting agent after the RCA products are filtered and before the amounts of RCA products are determined. In some embodiments, the RCA products may be labeled after the filtering step. Further, in some cases an image of the array need not be produced and stored. In these embodiments, the analysis of the array may be done during or immediately after imaging. In some embodiments in which analysis includes counting, the fluorescence detector used should be sufficient to resolve the different RCA products on the membrane. In some embodiments, the fluorescence detector may have a resolution of less than 10 um, e.g., less then 5 um or less than 1 um. In embodiments that involve measuring an aggregate signal, the fluorescence detector does not need to have such resolution.

In any embodiment, the pores of the capillary membrane should be of sufficient size so as to prevent the RCA products from passing through the pores. For example, in embodiments, the pore diameter of the capillary membrane may be no more than 50% of the median diameter of the RCA products, while in some embodiments it may be no more than 20% of the median diameter of the RCA products, and in some embodiments no more than 10% of the median diameter of the RCA products. As such, in filtering the sample using the porous capillary membrane, the RCA products should remain on top of the membrane and should not fully enter or pass through the pores.

In certain embodiments, the porous capillary membrane does not comprise a tethered capture agent (e.g., a tethered oligonucleotide, an antibody or streptavidin or the like) that specifically hybridizes with or binds to the RCA products. In these embodiments, the RCA products do not bind to the porous capillary membrane via a specific (e.g., a sequence-specific) interaction. In such embodiments, the porous capillary membrane does not comprise a plurality of different tethered sequence-specific capture agents (e.g., oligonucleotides) that are tethered to membrane at spatially addressable locations in the form of a microarray, as described in US2006022813.

In certain embodiments, other than the production of a light signal, no biochemical reactions (e.g., a reaction that results in the breakage or formation of a covalent bond) needs to take place on the membrane after the RCA products are filtered through the membrane.

As would be apparent, the rolling circle amplification (RCA) products are not denatured prior to being filtered through the membrane (e.g., not exposed to a temperature of at least 90° C. for at least 2 minutes).

Figure 2:
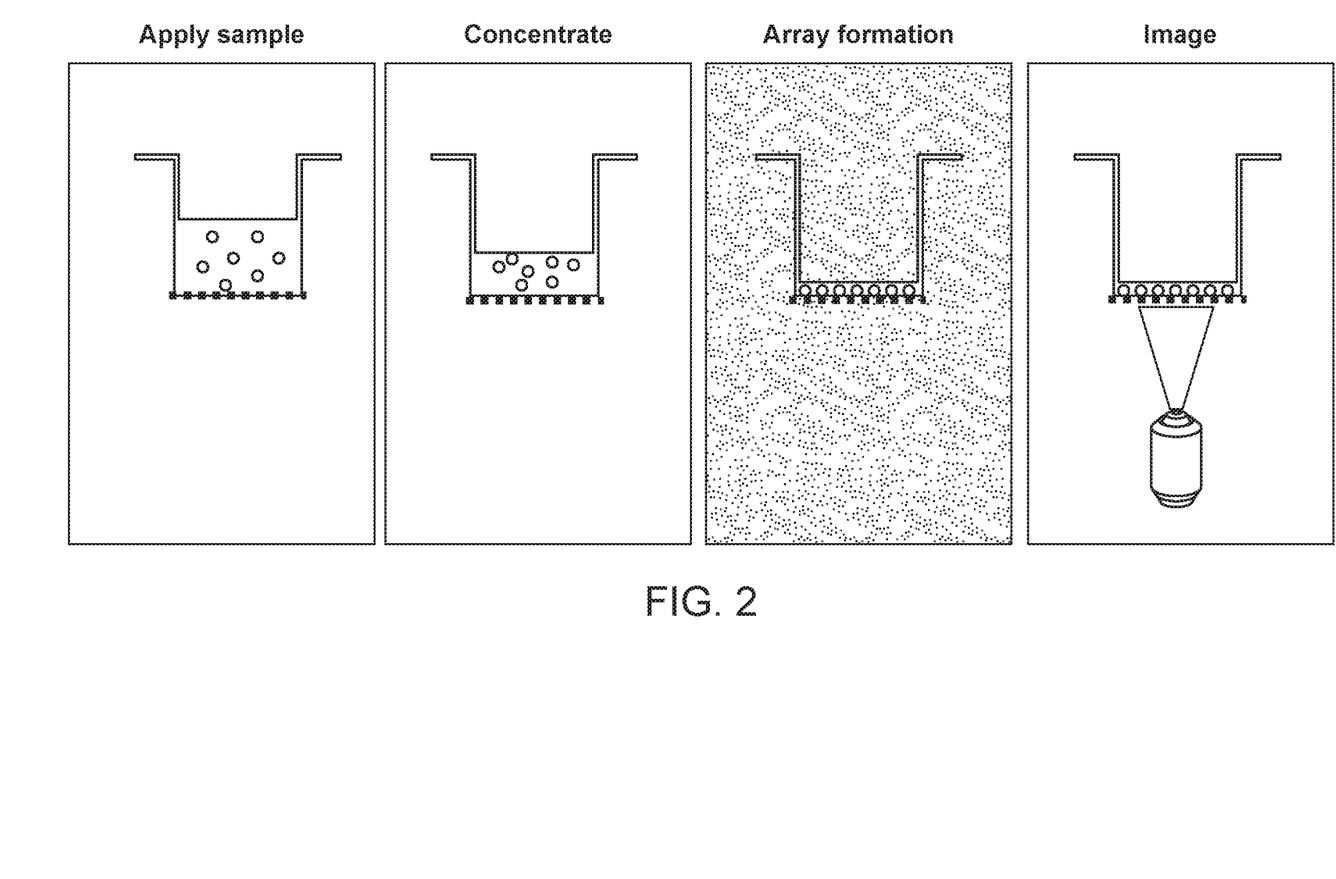
FIG. 2 schematically illustrates some of the principles of the present method.

FIG. 2 shows some of the principles of an exemplary embodiment the method. In the first step, a sample containing fluorescently labeled RCA products is placed into a container, e.g., a well that contains the membrane, e.g., as the bottom surface. The sample is concentrated by applying pressure that draws the liquid phase of the sample through the membrane. The RCA products are retained on the surface of the membrane in form of an array at a density of, e.g., at least 10, at least 50, at least 100, at least 500, at least 1,000, at least 5,000, or at least 10,000/mm$^2$. If the membrane is not already transparent, then, after addition of a wetting agent the membrane becomes transparent and the RCA products can be detected, e.g., imaged. The RCA products can also be fixed in place using a fixative, so that the membrane can be transported and/or stored so they can be re-read if a positive result is obtained. In some embodiments, the wetting agent, in addition to making the membrane transparent, also acts as a fixative. The array can be analyzed from either side of the membrane, e.g., through the membrane (as shown in FIG. 2). As would be apparent, if the membrane is read from "above", i.e., from the same side as the RCA products, the membrane does not need to be transparent. In some embodiments, the membrane may be dried before transport and analysis. The analyzed area may contain at least 10, e.g., at least 100, at least 1,000, at least 5,000, at least 10,000, at least 20,000, at least 50,000, at least 100,000, or at least 200,000 or more RCA products.

If desired, the RCA products can be labeled while they are bound to the membrane and, in certain embodiments, the membrane may be washed, e.g., with water or an aqueous buffer that contains salt, after the array of labeled RCA products has been produced and prior to analysis. This washing step may reduce background because potential sources of background (e.g., labeled nucleotides or labeled oligonucleotides that are not hybridized to an RCA product) can be washed through the filter and are not associated with the filter at the time the filter is analyzed. If necessary, other reagents, e.g., anti-fade or reagents that enhance fluorescence or the like, can be added to membrane prior to analysis in order to decrease background or increase the signal or the like. Likewise, if necessary, the labeled RCA products can be bound (covalently or non-covalently) to the membrane surface prior to analysis if necessary. Chemistries for linking biomolecules to a surface are well known and, in certain cases, the RCA products may be made using a modified nucleotide or a primer that has group that is specifically reactive with the surface of the membrane, thereby ensuring that only the RCA products become attached to the surface.

In certain embodiments, the filtering step is done by (i) placing the sample on the porous membrane; and (ii) applying a force that moves the sample through the membrane. The force applied to the sample may be an active force (e.g., a centrifugal force, a negative pressure or a positive pressure) or a passive force (e.g., via capillary action (using blotting paper, for example) or evaporation).

As noted above, the interior diameter of the pores in the membrane, the distance between the centers of adjacent pores in the membrane, and the distance between the edges of adjacent pores in the membrane can be controlled by the voltage of the deposition, the type of acid, and other parameters (see, generally, Poinern, supra). In some embodiments, the interior diameter of the pores in the membrane may be in the range of 5 nm to 500 nm, e.g., 4 nm to 250 nm, 4 nm to 50 nm, 50 nm to 100 nm, 100 nm to 200 nm or 200 nm to 500 nm. Independently, the average distance between the centers of adjacent pores in the membrane may be in the range of 50 nm to 1000 nm, e.g., 50 nm to 420 nm, 50 nm to 100 nm, 100 nm to 250 nm, 250 nm to 500 nm or 500 nm to 1000 nm. The average distance between the edges of adjacent pores in the membrane may be in the range of 10 nm to 500 nm, 10 nm to 50 nm, 50 nm to 200 nm, or 200 nm to 500 nm. It may be understood that the diameter and average distance values between pores provided herein are exemplary, and such values may vary based on the embodiment.

In some embodiments, the pore diameter and distance between the centers of adjacent pores may be optimized to provide labeled RCA products that are individually resolvable by the detection system used. Specifically, in certain cases, the pores in the membrane may have a relatively large diameter (e.g., a diameter in the range of 100 nm to 500 nm) and the average distance between the centers of adjacent pores in the membrane may be relatively large (e.g., in the range of 200 nm to 1000 nm, e.g., 200 nm to 420 nm), so that each of the labeled RCA products is pulled to the entrance to a pore (effectively "blocking" the pore) and the distance between adjacent labeled RCA products is resolvable by fluorescence microscopy. These optimal distances may be decreased if super resolution fluorescence microscopy (Huang et al, Annu. Rev. Biochem. 2009 78: 993-1016) is used.

The membrane used may be of any suitable thickness, e.g., in the range of 20 μm to 500 μm or 50 μm to 200 μm, as desired and, as noted above, may contain one or more support structures (e.g., a support ring) in order to maintain the integrity of the membrane during use.

As noted above, the present method may be used in protocols that require accurate quantification of the number of RCA products in a sample, particularly a sample that has a variable concentration of RCA products (e.g., from 10 to 10M that can be at a relatively low concentration e.g., 5,000 to 1M RCA products in a volume of 50 μl to 200 μl or more) and the statistical resolution required to identify a difference can only be reached only by counting at least 1,000, at least 5,000, at least 10,000, at least 50,000, at least 100,000 or at least 200,000 or more of the RCA products. As will be described in greater detail below, the method has particular use in copy number analysis and in non-invasive prenatal testing applications.

In some embodiments, the sample may contain multiple populations of RCA products (e.g., two, three or four or more populations of RCA products, such as a first population of labeled RCA products and a second population of RCA products), where the different populations of RCA products are distinguishably labeled, meaning that the individual members of each of the populations of RCA products labels can be independently detected and counted, even when the populations are mixed. Suitable distinguishable fluorescent label pairs useful in the subject methods include Cy-3 and Cy-5 (Amersham Inc., Piscataway, N.J.), Quasar 570 and Quasar 670 (Biosearch Technology, Novato Calif.), Alexafluor555 and Alexafluor647 (Molecular Probes, Eugene, Oreg.), BODIPY V-1002 and BODIPY V1005 (Molecular Probes, Eugene, Oreg.), POPO-3 and TOTO-3 (Molecular Probes, Eugene, Oreg.), and POPRO3 TOPRO3 (Molecular Probes, Eugene, Oreg.). Further suitable distinguishable detectable labels may be found in Kricka et al. (Ann Clin Biochem. 39:114-29, 2002). For example, the RCA products may be labeled with any combination of ATTO, ALEXA, CY, or dimeric cyanine dyes such as YOYO, TOTO etc. Further labels may also be included. Exemplary methods for making distinguishable populations of labeled RCA products are described in, e.g., PCT/US2014/06771, filed on Nov. 26, 2014 and PCT/US2014/067719, filed on Nov. 26, 2014, which are incorporated by reference herein for those teachings. In some cases, a population of RCA products can be distinguishably labeled by labeling it with multiple labels, thereby increasing the possibilities of multiplexing. For example, in some cases the RCA products of a population may be each labeled with two distinguishable dyes (e.g., both Cy3 and Cy5). When read, such dual-labeled RCA products will be distinguishable from RCA products that are labeled with an individual dye (e.g., Cy3 or Cy5).

In some embodiments, a first population of RCA products may represent a "test" population of labeled RCA products and a second population of RCA products may represent a "reference" population of RCA products to which the number of the first RCA products can be compared. For example, in some embodiments, the first population of RCA products may correspond to a first chromosomal region (e.g., a first chromosome such as chromosome 21) and the second population of RCA products may correspond to a second chromosomal region (e.g., a second chromosome such as chromosome 13 or 18 or a different region of the first chromosome) and the number of the first population of RCA products and the second population of RCA products can be counted and compared to determine if there is a difference in the copy number of the regions (indicating that there is duplication or deletion of the test region). In some embodiments, the sample contains at least a first population of RCA products and a second population of RCA products, wherein the first and second populations of labeled RCA products are distinguishably labeled in the labeling step. In these embodiments, the methods comprise determining the amount of (e.g., counting the number of) first labeled RCA products in an area of the membrane and determining the amount of (e.g., counting the number of) second labeled RCA products in an area (the same area or a different area) of the membrane, thereby providing an estimate of the amount of first and second populations of RCA products in the sample. This embodiment may further involve comparing the number of first RCA products in the sample to the number of second RCA products in the sample.

In some of these embodiments of the methods, the methods may comprise imaging the first and second populations of labeled RCA products to produce one or more images (e.g., one image or a first image and a second image, respectively) and, optionally, (i) determining the amount of labeled RCA products in the one or more images, thereby providing an estimate of the amount of first and second populations of labeled RCA products in the sample. The first and second populations of labeled RCA products can be separately detected using known methods (e.g., using appropriate filters etc.). The detection of RCA products can be done sequentially (in which embodiments, e.g., separate images for each label may be produced and the RCA products from each population may be analyzed sequentially. The detection of RCA products can also be done substantially simultaneously (in which embodiments, e.g., a single image that shows both populations of RCA products may be produced and the RCA products from each population may be analyzed at substantially the same time, i.e., substantially simultaneously. These embodiments of the methods may further comprise comparing amount of first labeled RCA products in the sample to the amount of second labeled RCA products in the sample. This step of the methods may involve counting at least 1,000 (e.g., at least 5,000, at least 10,000, at least 20,000, at least 50,000, at least 100,000, at least 500,000 up to 1M or more) labeled RCA products in the first population and counting at least 1,000 (e.g., at least 5,000, at least 10,000, at least 20,000 or at least 50,000, at least 100,000, at least 500,000 up to 1M or more) labeled RCA products in an area of the membrane, thereby ensuring that a difference in copy number can be called with statistical rigor.

In embodiments, the methods may further comprise detecting a difference between the amount of first RCA products in the sample to the amount of second RCA products in the sample, where the difference has a P-value of at least 0.95, at least 0.98 or at least 0.99. In some embodiments, the method can be used to detect at least a 1% difference, at least a 2% difference, at least a 3% difference, or at least a 5% difference, with a P-value of greater than 0.95, 0.98 or 0.99. For example, in embodiments involving a maternal sample from a pregnant female, the fetal fraction of the sample may be included in this calculation.

As noted above, in some cases the sample being analyzed using this method may be a sample of cell-free DNA obtained from blood, e.g., from the blood of a pregnant female. In these embodiments, the method may be used to detect chromosome abnormalities in the developing fetus (as described above) or to calculate the fraction of fetal DNA in the sample, for example. Copy number abnormalities that can be detected using the method include, but are not limited to, trisomy 21, trisomy 13, trisomy 18, trisomy 16, XXY, XYY, XXX, monosomy X, monosomy 21, monosomy 22, monosomy 16, and monosomy 15. Further copy number abnormalities that can be detected using the present method are listed in the following table.

Chromosome: Abnormality (Disease Association)
X: XO (Turner's Syndrome)
Y: XXY (Klinefelter Syndrome)
Y: XYY (Double Y Syndrome)
Y: XXX (Trisomy X Syndrome)
Y: XXXX (Four X Syndrome)
Y: Xp21 deletion (Duchenne's/Becker Syndrome, congenital adrenal hypoplasia, chronic granulomatus disease)
Y: Xp22 deletion (steroid sulfatase deficiency)
Y: Xq26 deletion (X-linked lymphoproliferative disease)
1: 1p somatic (neuroblastoma)
1: monosomy (neuroblastoma)
1: trisomy (neuroblastoma)
2: monosomy (growth retardation, developmental and mental delay, and minor physical abnormalities)
2: trisomy 2q (growth retardation, developmental and mental delay, and minor physical abnormalities)
3: monosomy (Non-Hodgkin's lymphoma)
3: trisomy somatic (Non-Hodgkin's lymphoma)
4: monosomy (Acute non lymphocytic leukemia (ANLL))
4: trisomy somatic (Acute non lymphocytic leukemia (ANLL))
5: 5p (Cri du chat; Lejeune syndrome)
5: 5q somatic (myelodysplastic syndrome)
5: monosomy (myelodysplastic syndrome)
5: trisomy (myelodysplastic syndrome)
6: monosomy (clear-cell sarcoma)
6: trisomy somatic (clear-cell sarcoma)
7: 7q11.23 deletion (William's syndrome)
7: monosomy (monosomy 7 syndrome of childhood; somatic: renal cortical adenomas; myelodysplastic syndrome)
7: trisomy (monosomy 7 syndrome of childhood; somatic: renal cortical adenomas; myelodysplastic syndrome)
8: 8q24.1 deletion (Langer-Giedon syndrome)
8: monosomy (myelodysplastic syndrome; Warkany syndrome; somatic: chronic myelogenous leukemia)
8: trisomy (myelodysplastic syndrome; Warkany syndrome; somatic: chronic myelogenous leukemia)
9: monosomy 9p (Alfi's syndrome)
9: monosomy 9p (Rethore syndrome)
9: partial trisomy (Rethore syndrome)
9: trisomy (complete trisomy 9 syndrome; mosaic trisomy 9 syndrome)
10: monosomy (ALL or ANLL)
10: trisomy somatic (ALL or ANLL)
11: 11p—(Aniridia; Wilms tumor)
11: 11q—(Jacobsen Syndrome)
11: monosomy (myeloid lineages affected (ANLL, MDS))
11: trisomy somatic (myeloid lineages affected (ANLL, MDS))
12: monosomy (CLL, Juvenile granulosa cell tumor (JGCT))
12: trisomy somatic (CLL, Juvenile granulosa cell tumor (JGCT))
13: 13q—(13q-syndrome; Orbeli syndrome)
13: 13q14 deletion (retinoblastoma)
13: monosomy (Patau's syndrome)
13: trisomy (Patau's syndrome)
14: monosomy (myeloid disorders (MDS, ANLL, atypical CML)
14: trisomy somatic (myeloid disorders (MDS, ANLL, atypical CML)
15: 15q11-q13 deletion (Prader-Willi, Angelman's syndrome)
15: monosomy (Prader-Willi, Angelman's syndrome)
15: trisomy somatic (myeloid and lymphoid lineages affected, e.g., MDS, ANLL, ALL, CLL)
16: 16q13.3 deletion (Rubenstein-Taybi)
16: monosomy (papillary renal cell carcinomas (malignant))
16: trisomy somatic (papillary renal cell carcinomas (malignant))
17: 17p—somatic (17p syndrome in myeloid malignancies)
17: 17q11.2 deletion (Smith-Magenis)
17: 17q13.3 (Miller-Dieker)
17: monosomy (renal cortical adenomas)
17: trisomy somatic (renal cortical adenomas)
17: 17p11.2-12 (Charcot-Marie Tooth Syndrome type 1; HNPP)
17: trisomy (Charcot-Marie Tooth Syndrome type 1; HNPP)
18: 18p—(18p partial monosomy syndrome or Grouchy Lamy Thieffry syndrome)
18: 18q—(Grouchy Lamy Salmon Landry Syndrome)
18: monosomy (Edwards syndrome)
18: trisomy (Edwards syndrome)
19: monosomy (Edwards syndrome)
19: trisomy (Edwards syndrome)
20: 20p—(trisomy 20p syndrome)
20: 20p11.2-12 deletion (Alagille)
20: 20q—(somatic: MDS, ANLL, polycythemia vera, chronic neutrophilic leukemia)
20: monosomy (papillary renal cell carcinomas (malignant))
20: trisomy somatic (papillary renal cell carcinomas (malignant))
21: monosomy (Down's syndrome)
21: trisomy (Down's syndrome)

22: 22q11.2 deletion (DiGeorge's syndrome, velocardiofacial syndrome, conotruncal anomaly face syndrome, autosomal dominant Opitz G/BBB syndrome, Caylor cardiofacial syndrome)
22: monosomy (complete trisomy 22 syndrome)
22: trisomy (complete trisomy 22 syndrome)

Exemplary methods for producing RCA products and labeling the same are describe in e.g., PCT/US2014/06771, filed on Nov. 26, 2014 and PCT/US2014/067719, filed on Nov. 26, 2014, which are incorporated by reference for disclosure of those methods.

Composition

A composition is also provided. In some embodiments the composition may comprise: a) a porous capillary membrane, e.g., a porous anodic aluminum oxide membrane; and b) an array of fluorescently labeled RCA products on a surface of the membrane. The array may comprises at least 1,000 labeled RCA products (e.g., at least 5,000, at least 10,000, at least 20,000, at least 50,000, at least 100,000, at least 500,000, or at least 1M labeled RCA products) and the labeled RCA products may be distributed across the surface of the membrane in a random manner at a density of, e.g., at least 10, at least 50, at least 100, at least 500, at least 1,000, at least 5,000, or at least 10,000/mm$^2$. As described above, the composition may comprise a porous capillary membrane; and at least two populations of fluorescently labeled RCA products on a surface of the membrane, where the different populations of fluorescently labeled RCA products are distinguishably labeled. Further details and variations of this composition may be found in the methods section of this disclosure.

Kits

Also provided by this disclosure are kits for practicing the subject methods, as described above. In some embodiments, a kit may contain at least: reagents for circularizing selected fragment in a sequence-specific manner and then performing rolling circle amplification of the circularized products. For example, one or more restriction enzymes, a ligase, and one or more oligonucleotide that can act as a splint to circularize the products, a strand-displacing polymerase for amplifying the circularized products by RCA, one or more labeled oligonucleotides for labeling the RCA products, and a porous capillary membrane, e.g., a porous anodic aluminum oxide membrane, as described above. The various components of the kit may be present in separate containers or certain compatible components may be pre-combined into a single container, as desired. Further details and variations of components of this kit may be found in the methods section of this disclosure.

In addition to the above-mentioned components, the subject kits may further include instructions for using the components of the kit to practice the subject methods, i.e., instructions for sample analysis. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

EMBODIMENTS

The following describes an exemplary implementation of the method.

In some embodiments, the method may comprise: (a) filtering a liquid sample containing fluorescently labeled rolling circle amplification (RCA) products using a porous anodic aluminum oxide membrane, thereby producing an array of the RCA products on the membrane; and b) determining the amount of labeled RCA products in the area of the membrane, thereby providing an estimate of the amount of the labeled RCA products in the sample. In some embodiments, the determining step may include counting the number of first and second labeled RCA products in the area. In other embodiments, the determining step may include detecting an aggregate signal from the area.

In embodiments, step (a) of the method may be done by: (i) placing the sample on the porous anodic aluminum oxide membrane; and (ii) applying a force that moves the sample through the membrane. In these embodiments, the force may be an active force (a centrifugal force, negative pressure or positive pressure) or a passive force (which may be applied by capillary action or evaporation). In some embodiments, the method may comprise washing the porous anodic aluminum oxide membrane between steps (a) and (b). In some embodiments, the determining step may comprise counting at least 1,000 labeled RCA products in the area of the image.

In embodiments, the interior diameter of the pores in the membrane may in the range of 5 nm to 500 nm and, independently, the average distance between the centers of adjacent pores in the membrane may be in the range of 50 nm to 1000 nm. In embodiments, the average distance between the edges of adjacent pores in the membrane may be in the range of 10 nm to 500 nm. In some embodiments, the sample may contain at least a first and a second population of labeled RCA products, wherein the first and second populations of labeled RCA products are distinguishably labeled. In these embodiments, the methods may further comprise imaging the first and second populations of labeled RCA products to produce one or more images (e.g., a first image and a second image, respectively). These methods may further comprise (i) counting the number of labeled RCA products in an area of the first image and (ii) separately counting the number of labeled RCA products an area, e.g., the same area, of the second image, thereby providing an estimate of the number of first and second populations of labeled RCA products in the sample. This embodiment may further comprise comparing the amount of first labeled RCA products in the sample to the amount of second labeled RCA products in the sample.

Also provided is a composition comprising: a) a porous capillary membrane; and b) an array of fluorescently labeled rolling circle amplification (RCA) products on a surface of the membrane. In some of these embodiments, the porous capillary membrane may be a porous anodic aluminum oxide membrane. In some embodiments, the array may comprise at least 1,000 RCA products. In some embodiments, the composition may comprise multiple arrays of fluorescently labeled RCA products, wherein the multiple arrays are on the surface of the membrane and distinguishably labeled. A description of each of these elements as well as optional elements that may be present in the composition may be found in the foregoing description.

Also provided is a kit comprising: a) a porous capillary membrane; and b) reagents for circularlizing DNA and performing rolling circle amplification (RCA); and c) reagents for labeling RCA products. A description of each of these elements as well as optional elements that may be present in the kit may be found in the foregoing description.

Embodiment 1 a method of sample analysis, comprising: (a) filtering a liquid sample containing rolling circle amplification (RCA) products through a porous transparent capillary membrane, thereby concentrating the RCA products and producing an array of the RCA products on the membrane; (b) fluorescently labeling the RCA products prior to or after step (a); and (c) counting the number of the individual labeled RCA products in an area of the membrane, thereby providing an estimate of the number of the labeled RCA products in the sample.

Embodiment 2

The method of Embodiment 1, wherein the porous transparent capillary membrane is a porous anodic aluminum oxide membrane.

Embodiment 3

The method of Embodiment 1 or 2, wherein step (b) is done by hybridizing fluorescently labeled oligonucleotides to the RCA products, prior to or after step (a).

Embodiment 4

The method of any prior Embodiment, wherein the method comprises imaging an area of the membrane to produce one or more images and counting the number of the individual labeled RCA products in the one or more images.

Embodiment 5

The method of any prior Embodiment, wherein step (a) is done by: (i) placing the sample on the porous transparent capillary membrane; and (ii) applying a force that moves the sample through the membrane.

Embodiment 6

The method of Embodiment 5, wherein the force is an active force or a passive force.

Embodiment 7

The method of Embodiment 6, wherein the active force is a centrifugal force, negative pressure or positive pressure.

Embodiment 8

The method of Embodiment 6, wherein the passive force is applied by capillary action or evaporation.

Embodiment 9

The method of any prior Embodiment, further comprising washing the porous transparent capillary membrane between steps (a) and (b).

Embodiment 10

The method of any prior Embodiment, wherein the counting step comprises counting at least 1,000 labeled RCA products in the area of the membrane.

Embodiment 11

The method of any prior Embodiment, wherein the interior diameter of the pores in the membrane is in the range of 2 nm to 500 nm.

Embodiment 12

The method of any prior Embodiment, wherein the average distance between the centers of adjacent pores in the membrane is in the range of 50 nm to 1000 nm.

Embodiment 13

The method of any prior Embodiment, wherein the average distance between the edges of adjacent pores in the membrane is in the range of 10 nm to 500 nm Embodiment 14

The method of any prior Embodiment, wherein the sample contains at least a first population of RCA products and a second populations of RCA products, wherein the first and second populations of labeled RCA products are distinguishably labeled in step (b).

Embodiment 15

The method of Embodiment 11, wherein the method comprises counting the number of first labeled RCA products in an area of the membrane and counting the number of second labeled RCA products in an area of the membrane, thereby providing an estimate of the number of first and second populations of RCA products in the sample.

Embodiment 16

The method of Embodiment 15, further comprising comparing the number of first RCA products in the sample to the number of second RCA products in the sample.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed.

Example 1

Use of an AAO Filter

Introduction

The first step in many molecular diagnostics applications is to convert a patient's biological material such as DNA into an effective biomarker. DNA is extracted, often purified and further converted to surrogate molecules, such as rolling circle products (RCPs), that can be measured or quantified. The detection of these surrogate molecules is frequently assisted by specific attachment of fluorescent dyes. Different dyes can attached to different surrogate markers, which enables multiplex detection even in complex mixtures. Deposition to planar surfaces, such as glass plates or slides, enables counting of the labeled molecules by microscopy or scanning.

A particular challenge comes when samples are low in concentration in a solution and it is difficult to deposit sufficient numbers of the molecules for accurate enumeration. Coating the glass slides with agents such as poly 1-lysine (PLL), amino-silanes or similar has proven an effective means of improving deposition for surrogate markers composed mostly of DNA (see, e.g., PCT/US2014/06771, filed on Nov. 26, 2014 and PCT/US2014/067719, filed on Nov. 26, 2014). This improves deposition efficiency to some degree, however many molecules remain in solution and are not included in subsequent analysis. In an effort to increase yield of deposition of fluorescently labeled biomarkers to a planar surface, the following filtration method was implemented.

Materials and Methods

Devices: Aluminum oxide membranes were bonded to well-plate super-structures that were either created in-house, or purchased from Ibidi (part #81201).

Amino-silane coated plates (96-Well Glass Bottom Plates SuperAmine, part #M96M) were purchased from ArrayIt Corporation.

Two separate rolling circle amplification products were created using methods previously described (PCT/US2014/06771). One RCA reaction was labeled by hybridization of a complementary detection oligonucleotide containing a 5' Atto 550 label, the other RCA reaction was labeled in a similar manner with 5' Atto 647N. The RCA reactions were mixed in a 50:50 mixture at 50 fM concentration.

For the glass plates, 100 ul of the reaction was aliquoted into 3 wells of the plate and allowed to incubate at room temperature for 16 hours. Another series of 3 wells were incubated for 90 seconds. Following the incubations, the wells were rinsed twice with 2xSSC and allowed to dry.

For the membranes, 100 ul samples were added to membrane-bottomed plates, and the plates were then placed on blotting paper (VWR part #28298-022). The samples passed through aluminum oxide membrane in approximately 90 seconds. The membrane-bottom plate was removed from the blotting paper, and 2 drops of prolong anti-fade reagent (Life Technologies) was added to each well to make them transparent.

Imaging was done for both formats on an Olympus X81 microscope with a 20× objective and a Hamamatsu Orca 4.0lt camera. Imaging was done by tiling 9×9 images to cover the entire bottom of each well. Images were analyzed and RCA products counted using in-house purpose-built software.

Results

Figure 3:
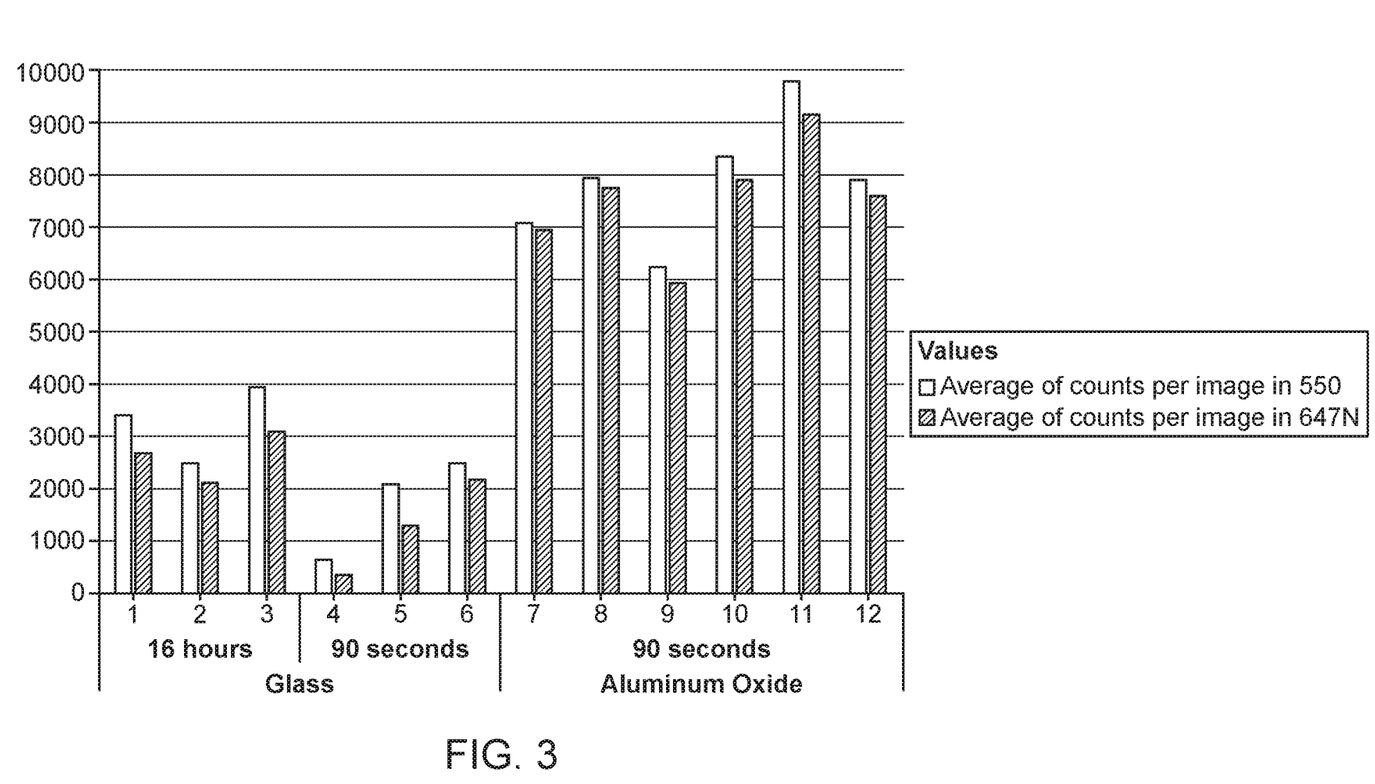
FIG. 3 is a graph depicting the number of counts per image on the y-axis, and the samples, incubation times, and glass or aluminum oxide plate type in the x-axis.

The results are summarized in FIG. 3. When incubated for 16 hours, deposition on the glass plates resulted in a per image average of 2,000 to 4,000 counts for the Atto 550 labeled RCA products. For the Atto 647N, average counts per image was between 2,000 to 3,000 counts. Incubation for 90 seconds on the glass plates resulted in a per image average count of between 500 to 2,500 counts for both channels. In contrast, incubation/deposition on the aluminum oxide plate resulted in a per image average of 6,000 to 10,000 counts for the Atto 550 labeled RCPs, and between 6,000 to 9,000 counts for the 647N labeled RCA products.

The data demonstrates that deposition on the aluminum oxide membrane results in roughly 4 times higher counts than when deposited on the glass plate for the same 90 second time interval. If incubation time is increased to 16 hours for the glass plate, the result is an increase of RCA products being detected on the glass plate, however still 2.5 times fewer than observed at 90 seconds on the aluminum oxide.

Example 2

Multiplex Detection Methods

Materials and Methods

Devices: Aluminum oxide membranes with 20 nm pores were bonded to 96 well-plate super-structures that were custom produced by 4titude Ltd, UK.

In this multiplex experiment, mixtures of DNA from 2 cell lines were used as the genetic starting material. The cell line DNA contained either 2 copies of chromosome 21 (normal genetic makeup) or cell lines containing 3 copies of chromosome (trisomy 21). DNA extracted from the cell lines was mixed in the following proportions 100:0, 95:5, 90:10, 0:100. Each DNA mixture was first digested using restriction enzymes, hybridized and ligated to a probe set, and subsequently enzymatically amplified by RCA as previously described (see WO2015083001 and WO2015083002). Two chromosome specific detection oligonucleotides (Atto 550 for Chromosome 18, Atto 647 for chromosome 21) were added to each sample and allowed to hybridize thus fluorescently labeling the chromosome specific RCA products in each sample.

Following labeling, 100 ul samples were added to membrane-bottomed plates, and the plates were then placed on a vacuum manfold (Supleco part #66879-U). The samples passed through aluminum oxide membrane in approximately 90 seconds. The membrane-bottom plate was washed twice with 400 ul 0.5xSSC, then allowed to dry. Three hundred microliters of wetting agent/fixative was then applied to each well to make them transparent and to fix the RCA products to the membrane.

Imaging was done on an Olympus X81 microscope with a 20× objective and a Hamamatsu Orca 4.0lt camera. Imaging was done by tiling 10×10 images to cover the entire bottom of each well. Images were analyzed and RCA products counted using in-house purpose-built software.

Results

Figure 4:
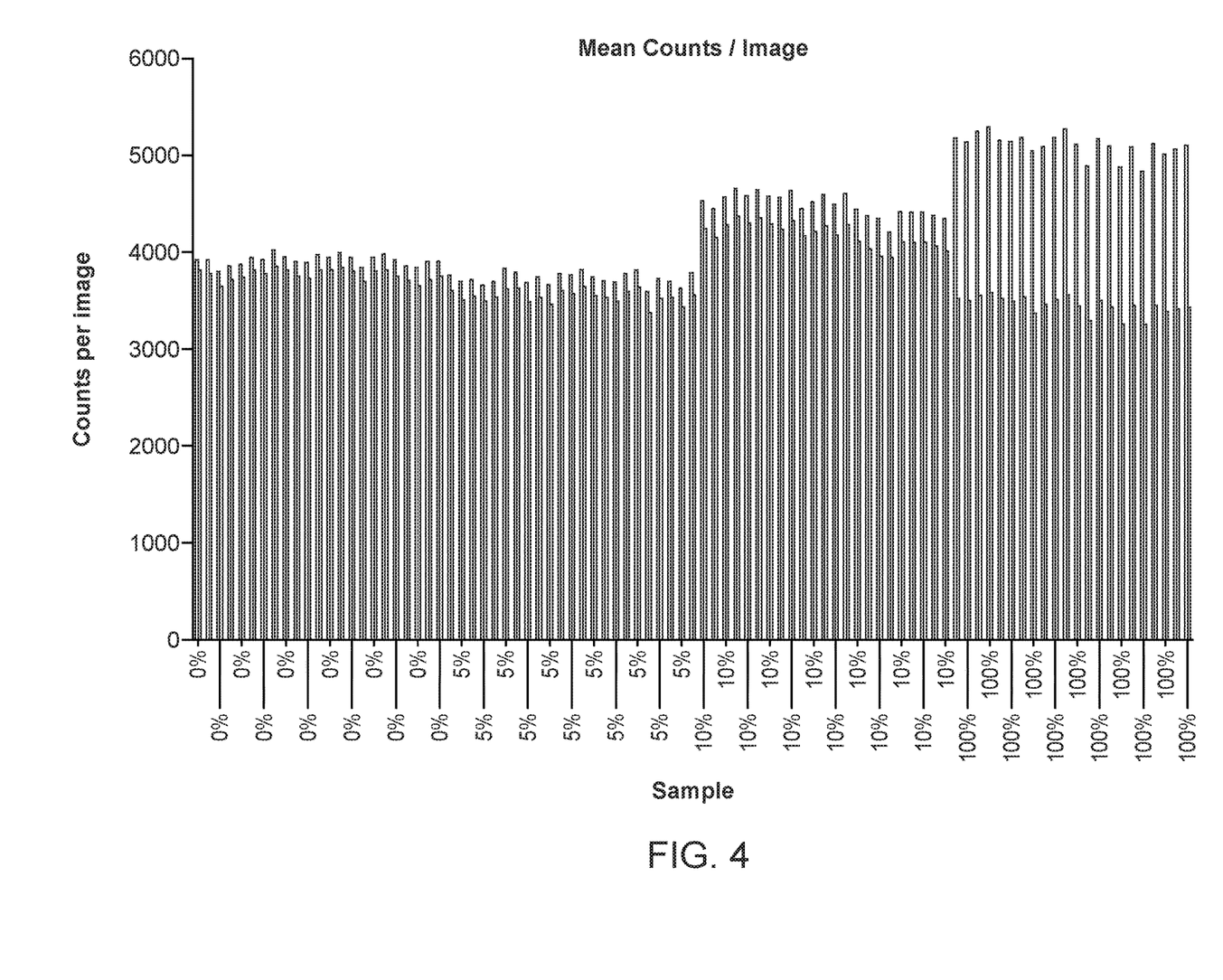
FIG. 4 is a histogram showing some of the results of the experiments described in Example 2.
Figure 5:
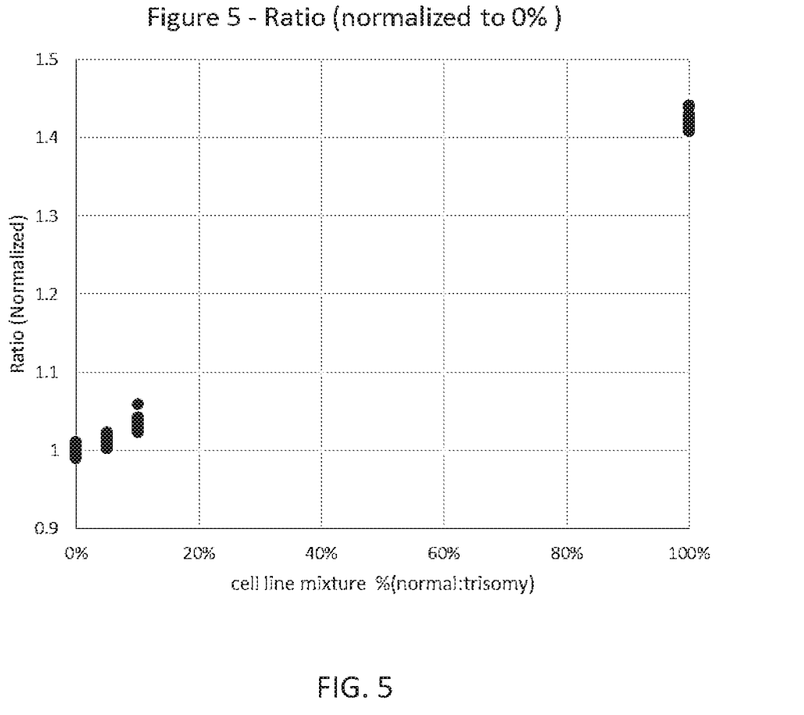
FIG. 5 is a plot of the ratios between the counts for two channels relative to the cell line mixture composition.

The results are summarized in FIG. 4. Average counts per image for all 91 samples included in the experiment ranged from 3000 to slightly over 5000 counts per image. The histograms clearly show a difference in proportion of counts between the 550 and 647 channels in the 0:100 ratio mixture (last 22 replicates), however it is more difficult to discern, from the figure alone, the proportion differences in the 0, 5, & 10% samples. FIG. 5 is a plot of the ratio between the counts for the two channels against cell line mixture composition. In this graph the trend is clearly represented, exemplifying the relative ratio shift in counts that follows the proportion of input cell line DNA samples.

The data demonstrates that deposition on the aluminum oxide membrane results in roughly 4 times higher counts than when deposited on the glass plate for the same 90 second time interval. If we increase the incubation time to 16 hours for the glass plate, the result is an increase of RCA products being detected on the glass plate, however still 2.5 times fewer than observed at 90 seconds on the aluminum oxide.

The invention claimed is:

1. A method of sample analysis, comprising:
   (a) producing a liquid sample comprising at least a first population of rolling circle amplification (RCA) products and a second population of RCA products, wherein the first and second populations of labeled RCA products are distinguishably labeled and the RCA products are not produced or labeled on or in a porous capillary membrane;
   (b) filtering the liquid sample through a porous capillary membrane, thereby depositing the RCA products on the membrane; and
   (c) determining the amount of the first labeled population of RCA products and the amount of the second labeled population of RCA products in an area of the membrane.

2. The method of claim 1, wherein the determining step (c) includes counting the numbers of first and second labeled RCA products in the area.

3. The method of claim 1, wherein the determining step (c) includes detecting an aggregate signal from the area.

4. The method of claim 1, wherein the porous capillary membrane is a porous anodic aluminum oxide membrane.

5. The method of claim 1, wherein the RCA products are distinguishably labeled by hybridizing fluorescently labeled oligonucleotides to the RCA products.

6. The method of claim 1, wherein the method comprises imaging the area of the membrane to produce one or more images and determining the number of the individual labeled RCA products in the one or more images.

7. The method of claim 1, wherein step (b) is done by:
   (i) placing the sample on the porous capillary membrane; and
   (ii) applying a force that moves the sample through the membrane.

8. The method of claim 7, wherein the force is an active force or a passive force.

9. The method of claim 8, wherein the active force is a centrifugal force, negative pressure or positive pressure.

10. The method of claim 8, wherein the passive force is applied by capillary action or evaporation.

11. The method of claim 1, further comprising washing the porous capillary membrane between steps (b) and (c).

12. The method of claim 1, wherein the determining step (c) comprises counting at least 1,000 labeled RCA products in the area of the membrane.

13. The method of claim 1, wherein the interior diameter of the pores in the membrane is in the range of 2 nm to 500 nm.

14. The method of claim 1, wherein the average distance between the centers of adjacent pores in the membrane is in the range of 50 nm to 1000 nm.

15. The method of claim 1, wherein the average distance between the edges of adjacent pores in the membrane is in the range of 10 nm to 500 nm.

16. The method of claim 1, further comprising comparing the amount of first RCA products in the sample to the amount of second RCA products in the sample.

17. The method of claim 1, wherein the porous capillary membrane is made transparent using a wetting agent between steps (b) and (c).

18. A method of sample analysis, comprising:
   (a) producing a liquid sample comprising at least a first population of rolling circle amplification (RCA) products and a second population of RCA products, wherein the first and second populations of labeled RCA products are distinguishably labeled and the RCA products are not produced or labeled on or in a capture support;
   (b) filtering the liquid sample through a capture support that acts as a filter for the RCA products, thereby depositing the RCA products on the capture support; and
   (c) determining the amount of the first labeled population of RCA products and the amount of the second labeled population of RCA products in an area of the capture support.

19. The method of claim 18, where determining step (c) includes counting the numbers of first and second labeled RCA products in the area.

20. The method of claim 18, where determining step (c) includes detecting an aggregate signal from the area.

* * * * *